United States Patent [19]
Putnam

[11] Patent Number: 5,382,163
[45] Date of Patent: Jan. 17, 1995

[54] METHOD AND APPARATUS FOR DETECTING THE PRESENCE OF DENTAL PLAQUE OR CALCULUS

[76] Inventor: David L. Putnam, 21806 NE. 1st, Redmond, Wash. 98053

[21] Appl. No.: 916,382

[22] Filed: Jul. 20, 1992

[51] Int. Cl.$^6$ .................................................. A61C 5/00
[52] U.S. Cl. ....................................... 433/215; 433/29; 128/665
[58] Field of Search .................. 433/29, 215, 229; 128/777, 665, 634; 356/317, 318, 341

[56] References Cited

U.S. PATENT DOCUMENTS

| | | | |
|---|---|---|---|
| 3,709,612 | 1/1973 | Clemens | 356/178 |
| 3,811,777 | 5/1974 | Chance | 356/73 |
| 4,170,987 | 10/1979 | Anselmo et al. | 128/665 |
| 4,178,917 | 12/1979 | Shapiro | 128/665 |
| 4,290,433 | 9/1981 | Alfano | 128/665 |
| 4,479,499 | 10/1984 | Alfano | 433/29 |
| 4,515,476 | 5/1985 | Ingmar | 128/665 |

FOREIGN PATENT DOCUMENTS 0113152  7/1984  European Pat. Off. ............ 128/665

*Primary Examiner*—Cary E. O'Connor
*Attorney, Agent, or Firm*—Seed and Berry

[57] ABSTRACT

A method and apparatus for detecting dental plaque or calculus deposits on a tooth site using a pulse of broad band light to illuminate a tooth site thereby exciting the deposit to luminescence. A time-related characteristic of the luminescence, such as its decay rate, is then analyzed to detect the presence of plaque or calculus at the tooth site. The excitation radiation preferably encompasses a range of wavelengths between about 375 nm to 575 nm, and the time-related characteristic of the luminescence that is analyzed preferably has a wavelength above about 600 nm.

28 Claims, 5 Drawing Sheets

METHOD AND APPARATUS FOR DETECTING THE PRESENCE OF DENTAL PLAQUE OR CALCULUS

TECHNICAL FIELD

This invention relates to dental care, and more particularly, to a method and apparatus for detecting dental and/or mineralized dental plaque.

BACKGROUND OF THE INVENTION

The accumulation of dental calculus and its precursor, dental plaque, on tooth surfaces is a common dental problem. Dental calculus occurs because of the interaction between bacterial plaque and the host site. Dental calculus occurs both on visible surfaces of the tooth as well as hidden surfaces, such as the subgingival surface of the tooth and ultimately the root within periodontal pockets.

Calculus is essentially mineralized calcified plaque. Mature calculus consists of approximately 15%-20% organic material, and the remainder is mineral salts. The minerals, predominantly calcium and phosphates, are deposited in an organic matrix. The mineral content of calculus spans a wide range of components, from hydroxyapatite, to magnesium, potassium and trace components such as fluoride, zinc and strontium. Differences in the organic and inorganic composition of saliva and crevicular fluids or inflammatory exudates in contact with supragingival and subgingival plaque, respectively, account in large part for notable differences in the types of calculus which form in the supra- or subgingival environment.

Periodontal therapy is based upon the daily removal of bacterial plaque by the patient, and the removal of plaque, calculus and other oral debris by the periodontal therapist. The success of therapy, therefore, is dependent upon the identification and thorough removal of plaque and calculus and associated root contaminants. This is usually accomplished through a variety of different procedures, such as scaling and root planing, or through periodontal surgical procedures.

Dental calculus and other contaminants are currently identified through a variety of means. Plaque and dental calculus located on visible surfaces of the tooth can usually be seen quite easily during a dental examination. However, subgingival plaque and calculus in the periodontal pocket can be identified only by probing and exploration of the periodontal pocket by the therapist using various manual instruments. This process is laborious, and it is complicated by a great variation in local anatomy of the periodontium. Also, conventional tactile detection by hand probing is subject to limitations and error. Calculus may be present but go undetected, thus untreated. Conversely, false-positive diagnoses may lead to execution of unwarranted and costly removal procedures. Natural anomalies of teeth sometimes present difficulty to tactile probing. Practitioner time and effort may be wasted on asserting the nature of a questionable source and trying to remove it.

Detection of subgingival plaque and calculus becomes even more difficult as the severity of periodontal disease increases—a situation that makes detection of plaque and calculus even more important. Increasing periodontal disease and the resulting deepening in the periodontal pocket not only affect the ability to identify the plaque and calculus, but they also exert a profound effect upon the ability to remove these deposits by instrumentation. An additional complication is the fact that dental calculus may be deposited in areas of reabsorption of the root surface. Current methods of detection do not adequately differentiate between calculus and root roughness which has no clinical significance. Detection of subgingival calculus by nontactile means, such as by the use of X-rays, is also inadequate.

It has been claimed that dental caries can be detected optically. For example, Alfano U.S. Pat. Nos. 4,479,499 and RE 31,815 disclose a method and apparatus for detecting caries by illuminating a potential caries site with monochromatic light, and visible light emitted from the site is examined to provide an indication of the presence of caries at the site. Ingmar U.S. Pat. No. 4,515,426 similarly discloses a device for optically detecting caries in which a site is illuminated by a light having a predetermined wavelength or range, and the luminescent properties of light emitted at the site are examined to detect the presence of caries. Alfano U.S. Pat. No. 4,930,516 et al. discloses a method for detecting cancerous tissue using an optical technique similar to the technique used to detect caries in U.S. Pat. No. 4,479,499. Kittrell U.S. Pat. No. 4,718,417 et al. discloses a method of diagnosing arterial plaque in which light having a wavelength of about 480 nm is conducted through an optical fiber to an arterial site, and scattered light and fluorescence light from the site are returned through the optical fiber where they are analyzed to determine the presence of arterial plaque at the site.

An article by R. R. Alfano et al. entitled *Medical Diagnostics: A New Optical Frontier* in the Dec. 1985 edition of PHOTONICS SPECTRA, describes the use of luminescence spectroscopy to diagnose a variety of abnormal human conditions including tooth decay, cancer, and arteriosclerosis.

An article by J. Brinkmen et al. entitled *Optical Quantitation of Natural Caries in Smooth Surfaces of Extracted Teeth* in a 1988 edition of BASIC SCIENCES describes a system for optically detecting caries by separately illuminating a carious and a non-carious region of a tooth and comparing the light reflected from each region.

An abstract of a conference presentation by J. J.ten Bosch et al. given at the Jul. 3–6, 1985 conference of the Congress of European Organization for Caries Research in Stenungssund, Sweden and published in CALCIFIED TISSUE ABSTRACT, vol. 19, no. 2, p. 115, describes a luminescence technique for detecting caries.

An abstract of an article by J. J.ten Bosch et al. in 6 Swedish Dental Journal 1–7 (1982) entitled *Long-Wavelength Fluorescence of Bovine Tooth Components* published in ABSTRACTS FROM THE 32ND ORCA CONGRESS no. 106 also describes a luminescence technique for detecting caries.

The above-described prior art devices and publications have a number of features in common. First, they illuminate the site with monochromatic or narrow band light. Second, the light returned from the site is analyzed by measuring its amplitude at two wavelengths. Finally, none of the prior art patents and publications even recognize that dental plaque or calculus can be detected optically based on the luminescence properties of the deposit.

A sensor that could optically detect plaque and calculus would remove the uncertainty of tactile probing and would greatly increase the efficiency and effectiveness of basic dental care.

SUMMARY OF THE INVENTION

It is an object of the invention to provide a method for determining whether or not plaque and calculus are present on teeth, thus confirming the need for treatment.

It is another object of the invention to provide a method and apparatus for confirming after treatment that plaque and calculus has, in fact, been removed from teeth surfaces.

It is another object of the invention to provide a method and apparatus for detecting plaque and calculus subgingivally where visual assessment is not possible.

It is still another object of the invention to provide a method for optically detecting plaque and calculus that is quick and easy to use even by relatively untrained practitioners.

These and other objects of the invention are provided by a method and apparatus for detecting the presence of dental plaque or calculus at a tooth site. A first electromagnetic radiation having a predetermined characteristic illuminates the site and causes a second electromagnetic radiation to be emitted from the site if dental plaque or calculus is present. A predetermined characteristic of the second electromagnetic radiation is then analyzed to detect the presence of dental plaque or calculus at the site.

The first electromagnetic radiation may assume a variety of forms, such as a pulse of electromagnetic radiation or electromagnetic radiation amplitude modulated at a predetermined frequency. Although the first electromagnetic radiation may be monochromatic or polychromatic, it preferably encompasses a relatively broad band of wavelengths such as between about 375 nm to 575 nm. Electromagnetic radiation having this characteristic may be generated by band-pass filtering electromagnetic radiation having a broad range of wavelengths encompassing the range of between approximately 375 nm to 575 nm. The second electromagnetic radiation is also preferably passed through an optical filter prior to being analyzed. An optical filter passing electromagnetic radiation having wavelengths greater than approximately 600 nm is satisfactory.

A variety of characteristics of the second electromagnetic radiation may be analyzed, including time-related characteristic and an intensity-related characteristic. The time-related characteristic may be a predetermined phosphorescent emission decay characteristic of the second electromagnetic radiation after the termination of the first electromagnetic radiation For example, the rate of decay during a predetermined period may be used. If amplitude modulated electromagnetic radiation is used to illuminate, the site, the second electromagnetic radiation will also be amplitude modulated at the same frequency if dental plaque or calculus are present at the site. The time-related characteristic may then be the difference between the phase of the amplitude modulation of the first electromagnetic radiation and the phase of the amplitude modulation of the second electromagnetic radiation.

DETAILED DESCRIPTION OF THE INVENTION

Figure 1:
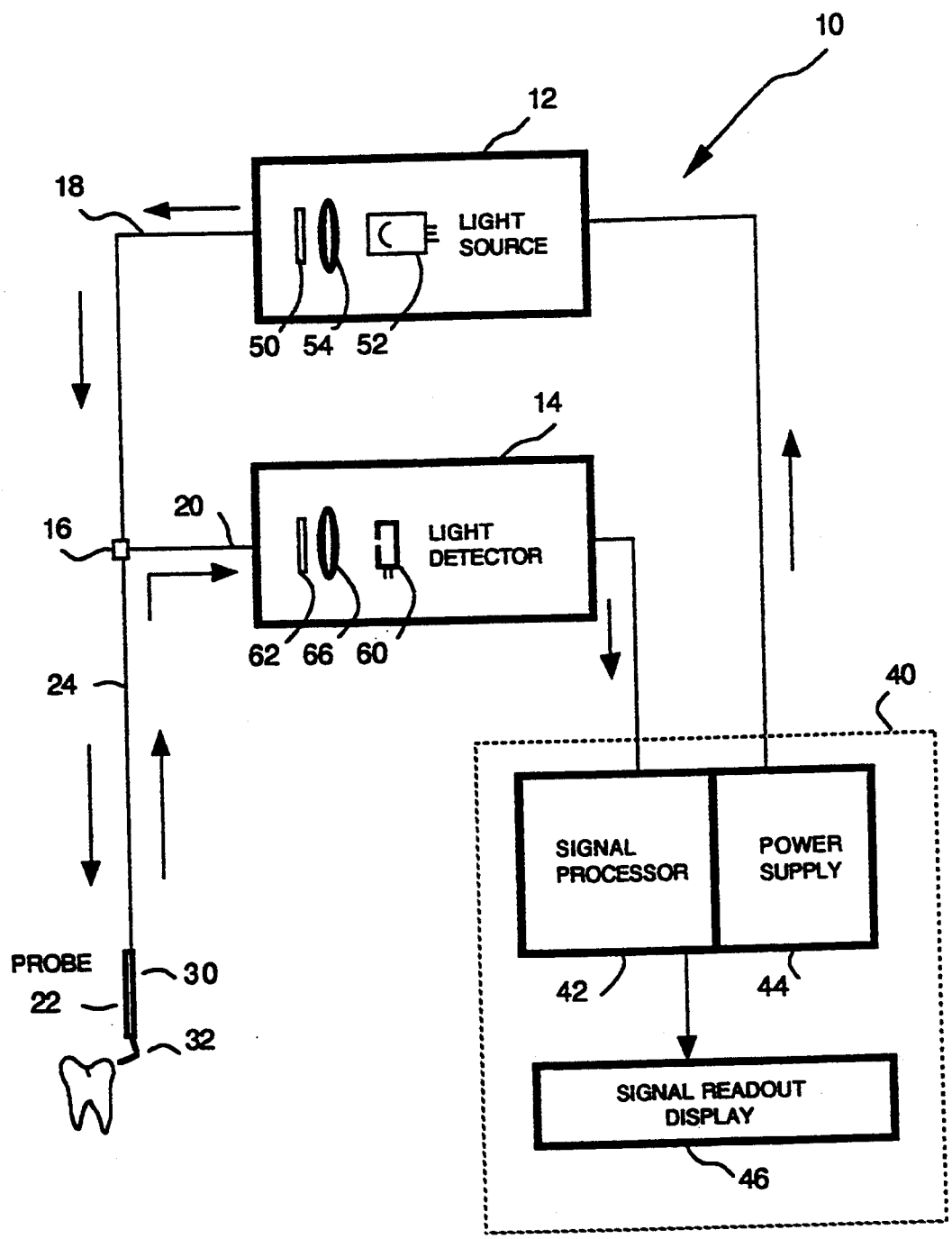
FIG. 1 is a block diagram of one embodiment of the inventive method and apparatus for detecting the presence of dental plaque or calculus at a tooth site.

A block diagram of one embodiment of the inventive method and apparatus for detecting plaque and calculus is illustrated in FIG. 1. The system 10 includes a light source subsystem 12 and a light detector subsystem 14. The light source subsystem 12 and light detector subsystem 14 are connected to a light splitter/combiner 16 through respective fiberoptic waveguides 18, 20. A probe 22 is optically coupled to the light splitter/combiner 16 by still another fiberoptic waveguide 24. The probe 22 may assume a variety of forms. However, it may include a cylindrical handgrip 30 and tubular probe tip 32 through which the fiberoptic waveguide 24 extends so that the end of the fiberoptic waveguide 24 is exposed at the end of the probe tip 32. The probe 22 may also be incorporated in a conventional dental tool for removing plaque or calculus so that it will signal when all of the plaque or calculus has been removed during a cleaning procedure. Although the embodiment of FIG. 1 uses fiberoptic waveguides 18-24 to convey light, it will be understood that other conventional devices for conveying light may also be used.

The light source subsystem 12 and light detector subsystem 14 are operated by a control subsystem 40 which includes a signal processor (described in greater detail below), a source power circuit (which may be simply a power driver circuit) triggered by the signal processor 42, and a signal readout 46 of conventional design.

The light source subsystem 12 may include a variety of light sources 52. For example, the light source 52 may be a conventional xenon flash lamp which is triggered by the source power circuitry 44 upon receipt of a trigger signal from the signal processor 42. The relatively broad band light pulse from the xenon flash tube is then coupled through fiberoptic waveguide 18, combiner 16 and fiberoptic waveguide 24 to a tooth site which may contain plaque or calculus. The optical pulse illuminates the tooth surface. If calculus or plaque is present, the radiation ,excites it to luminesce. A characteristic of the light signal returned from the tooth site thus depends upon the presence absence of calculus or plaque. The light from the tooth site is coupled through the fiberoptic waveguide 24, splitter/combiner 16 and fiberoptic waveguide 20 to the light detector subsystem 14. The light detector subsystem 14 generates an electrical signal indicative of the intensity of the light. This signal is then analyzed by the signal processor 42 to determine the presence or absence plaque or calculus at the tooth site.

The signal processor 42 may analyze the returned signal in a variety of manners. Generally, the decay of the returned signal after the optical pulse will be slower when plaque or calculus is present at the tooth site. The signal processor 42 may analyze a time-dependent characteristic of the returned signal. e.g., the rate of signal decay as a function of time. An intensity-related characteristic of the luminescence signal may also be analyzed. Since the returned signal in the presence of plaque or calculus at the tooth site has a time-dependent decay, the intensity of the returned signal will be greater during a predetermined period after the optical pulse in the event that plaque or calculus is present at the tooth site.

The light from the light source 52 in the light source subsystem 12 may also be a conventional source of continuous electromagnetic radiation that has been amplitude modulated at a predetermined frequency. This amplitude modulated radiation will then illuminate the tooth site in a correspondingly modulated manner so that the returned signal will also be amplitude modulated at the same frequency. However, the phase of the returned signal will be shifted from the phase of the illuminating radiation by an amount that is a function of the magnitude of the luminescence caused by the presence of plaque or calculus. A greater luminescence will produce a greater phase shift, and the magnitude of the phase shift can thus be analyzed by the signal processor 42 to determine the presence or absence of plaque or calculus at a tooth site.

Although a broad band source of electromagnetic radiation is preferably used as the light source 52, the band is preferably limited to a predetermined range of wavelengths by placing an optical filter 50 between the light source 52 and the fiberoptic waveguide 18. In the preferred embodiment, the optical filter will pass light having wavelengths between about 375–575 nm. A lens 54 of conventional design may be positioned between the light source 52 and the filter 50. Although light of between about 375–575 nm is preferably used, monochromatic light, such as generated by a light-emitting diode, laser diode or a laser, may also be used either within or without the 375–575 nm range of wavelengths. Similarly, polychromatic radiation (i.e., light at two or more distinct wavelengths), either within or without the 375–575 nm band may also be used.

A variety of light detectors 60 in the light detector subsystem 14 may also be used. The light detector 60 may be a photomultiplier tube of conventional design or a conventional photodiode or phototransistor. An optical filter 62 may be positioned between the fiberoptic waveguide 20 and the light detector 60. The filter 62 preferably passes light having wavelengths that are greater than about 600 nm. Once again, a lens 66 may be positioned between the filter 64 and the light detector 60.

In operation, either pulsed or continuous light generated by the light source subsystem 12 is coupled to a tooth side using, for example, the fiberoptic waveguide 18, splitter/combiner 16 and fiberoptic waveguide 24. The electromagnetic radiation from the light source subsystem 12 excites the tooth site, and the electromagnetic radiation from the resulting luminescence is coupled through fiberoptic waveguide 24, splitter/combiner 16, and fiberoptic waveguide 20 to the light detector subsystem 14. The light detector subsystem 14 then generates an luminescence signal that is applied to the signal processor 42. The signal processor 42 analyzes a predetermined characteristic of the luminescence signal (e.g., slope, phase shift, or amplitude) to determine if plaque or calculus is present at the tooth site being examined.

Figure 2:
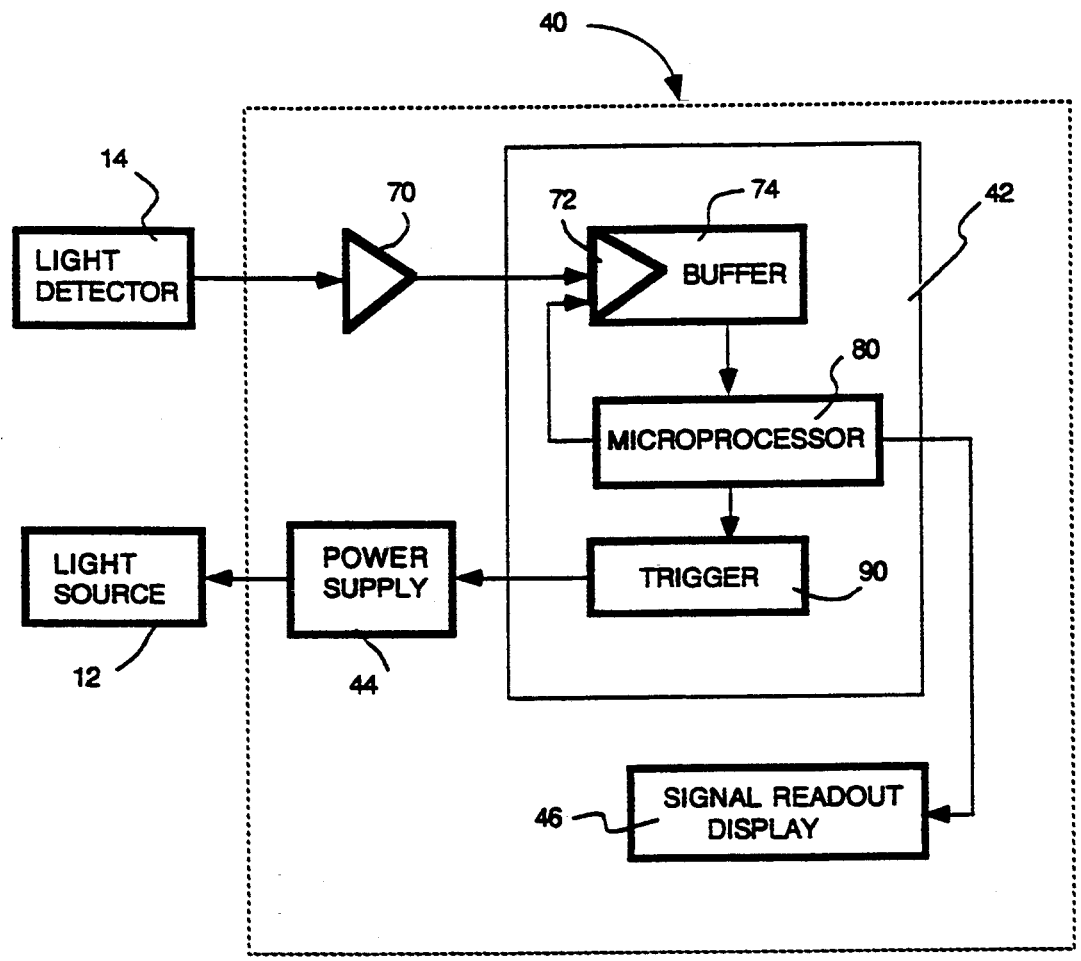
FIG. 2 is a block diagram of a signal processor used in the embodiment of FIG. 1.

The control subsystem 40 is illustrated in greater detail in FIG. 2 along with the light source subsystem 12 and light detector subsystem 14. As illustrated in FIG. 2, the output of the light detector subsystem 14 is boosted by an amplifier 70 of conventional design. The analog signal at the output of the amplifier 70 is then sampled by an analog-to-digital convertor 72 of conventional design, and the resulting digital words indicative of the samples are stored in a buffer 74. The buffer 74 stores all of the samples used to determine the presence or absence of plaque or calculus at a tooth site. A microprocessor 80 programmed with software described below reads the samples stored in the buffer 74 when the signal from the light detector subsystem 14 is to be analyzed. The microprocessor 80 then provides an output to a display 46 of conventional design. The output may be in the form of a digital word indicative of either a parameter of the luminescence signal or a value corresponding to the probability or amount of plaque or calculus present at the site. This digital word is displayed as a number on the display 46. Alternatively, the microprocessor 80 may output a single bit that merely triggers a light or sound in the display 46 if plaque or calculus is considered to be present at the site.

The microprocessor 80 also provides a trigger signal to a trigger generator 90 of conventional design. The trigger generator may be, for example, a conventional one-shot. The trigger generator 90 provides a signal to a conventional power supply 44 which generates a relatively high power output for a period of time determined by the trigger generator 90. The output of the power supply 40 either causes the light source subsystem 12 to generate a pulse of electromagnetic radiation or an amplitude modulated continuous electromagnetic radiation. The trigger signal output by the trigger generator 90 is also applied to the analog-to-digital convertor 72 to inform the convertor 72 that a flash has been generated so that the conversion can begin.

Figure 3:
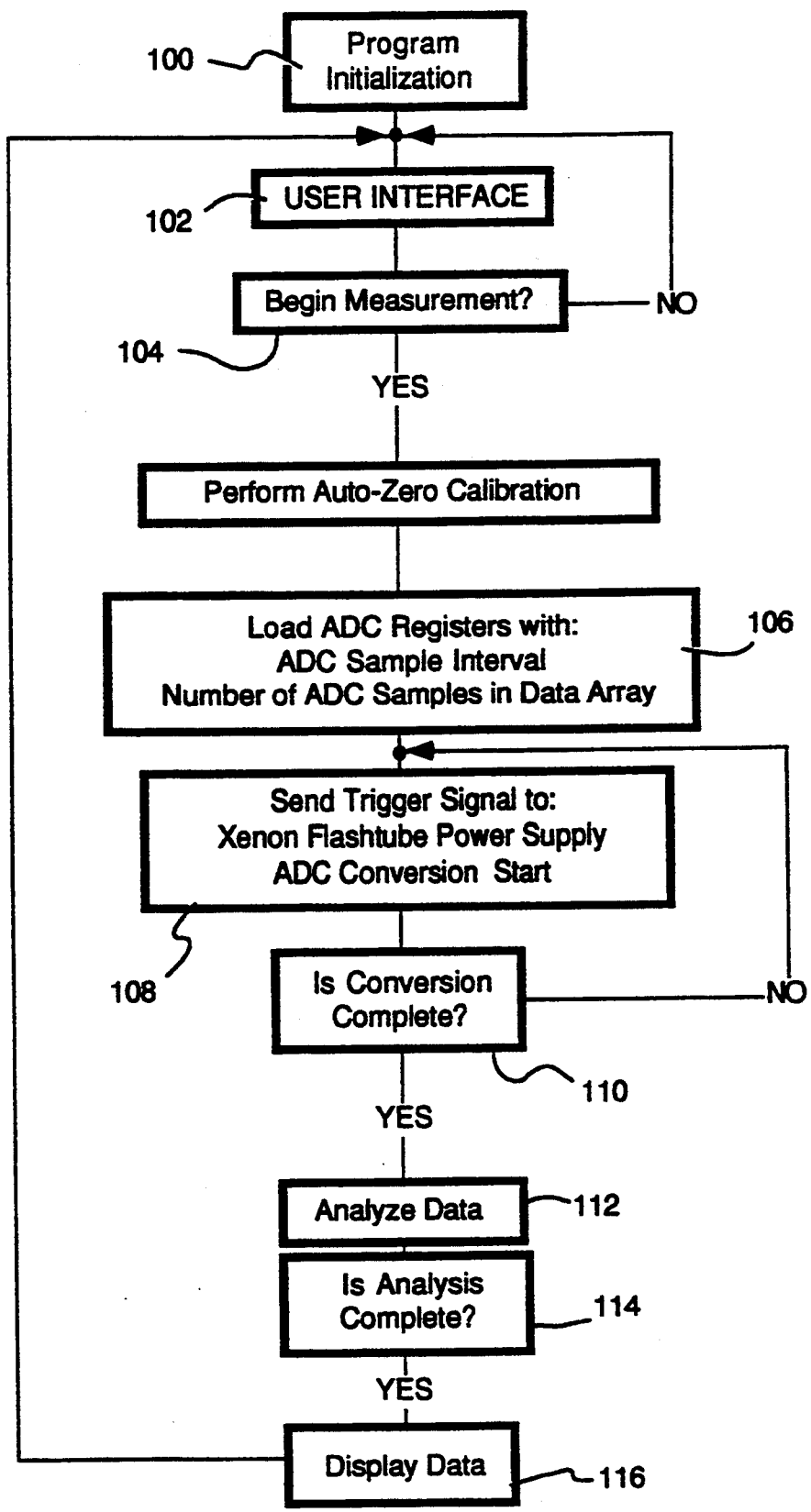
FIG. 3 is a flow chart of the software controlling the operation of a computer used in the signal processor of FIG. 2.

A flow chart of the software for controlling the operation of the microprocessor 80 is illustrated in FIG. 3. The program starts at 100, in which various registers, flags and buffers, including buffer 74, are initialized. The microprocessor 80 then checks a conventional user interface 102, such as a trigger switch (not shown), which is actuated by the user to indicate that a measurement should begin. The status of the user interface 102 is checked at 104. If the user interface 102 has not been actuated, the software in the microprocessor 80 remains in the loop through 102 and 104. If the user interface 102 has been actuated, the program progresses to 106, where the analog-to-digital convertor 72 is loaded by the microprocessor 80 with the interval during which samples are to be taken and the number of samples to be taken during that interval. The microprocessor 80 then applies a trigger signal to the trigger generator 90 at 108. The power supply 44 causes the light source subsystem 12, such as a xenon flash tube, to generate a pulse of electromagnetic radiation. The microprocessor 80 also triggers the analog-to-digital convertor 72 at 108 to start the analog-to-digital conversion.

After the tooth site has been illuminated, the analog-to-digital convertor 72 takes a series of samples which are stored in the buffer 74, as explained above. During this time, the microprocessor 80 checks to determine when the sampling and conversion has been completed. This function is performed at step 110. If the sampling and conversion has not been completed, the program returns to 108 to generate another flash from the light source 12. When the sampling and conversion is complete, the program progresses to 112 where the data in the buffer 74 are analyzed using a variety of mathematical calculations. More specifically, during step 112 the microprocessor 80 normalizes the accumulated values at each time interval of sample reading in the buffer taken during the sampling period. The microprocessor 80 also calculates the rate at which the returned signal decays as a function of time during a predetermined period. Completion of the analysis occurring at 112 is detected at 114. When the analysis has been completed, the data calculated during the analysis is output to the display at 116. The program then returns to 102 to sample the user interface for a subsequent measurement, as explained above.

Figure 4:
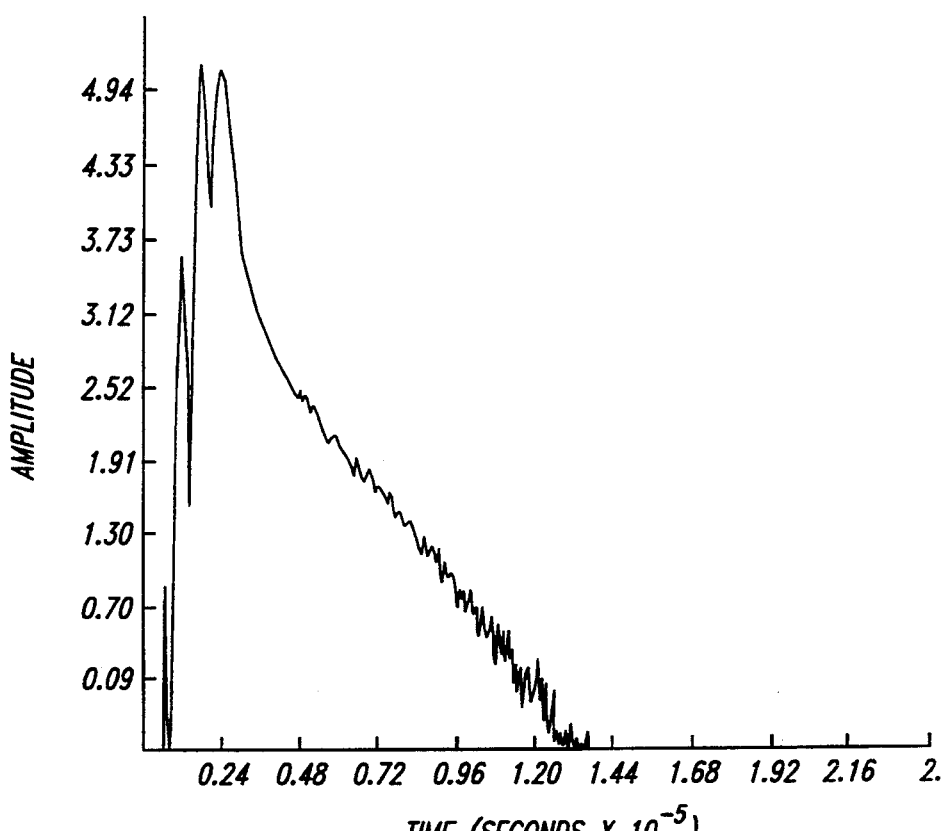
FIG. 4 is a graph of the intensity of electromagnetic radiation as a function of time from a probe used in the embodiment of FIG. 1 when the probe is not in contact with a tooth site.

A graph of the signal from the light detector subsystem 14 as a function of time is illustrated in FIG. 4. The graph depicts the returned signal when the probe tip 32 is not in contact with a tooth site. The graph shows the luminescence signal quickly building to a peak during the pulse of electromagnetic radiation from the light source subsystem 12. The returned signal then decays at a rate that is probably a function of the system response time. Although the illuminating light terminates very quickly, the detector system has a relatively low-frequency response, thus making it incapable of following the termination of the illumination light.

Figure 5:
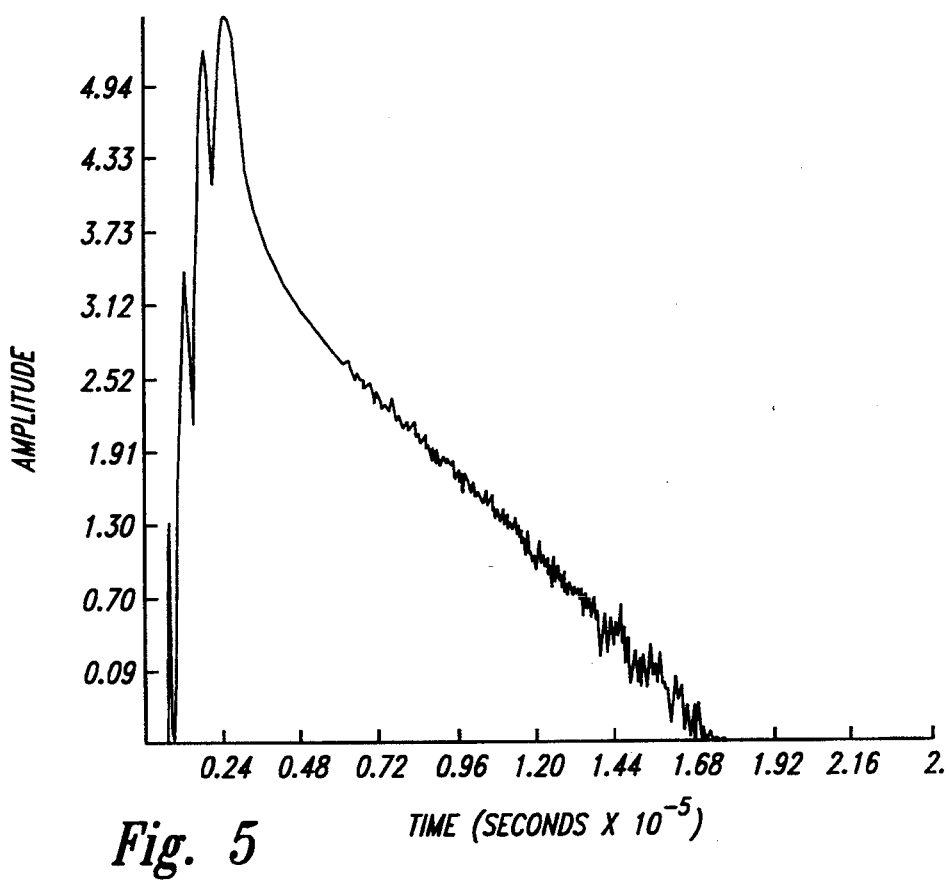
FIG. 5 is a graph of the intensity of electromagnetic radiation as a function of time from a probe used in the embodiment of FIG. 1 when the probe is in contact with a tooth site that does not contain plaque or calculus.

FIG. 5 shows the signal from the light detector subsystem 14 when the probe tip 32 is placed in contact with a tooth site in which plaque or calculus is not present. It is apparent from a comparison of FIGS. 4 and 5, that the decay of the returned signal is slower when the tip 32 is placed in contact with a tooth. This phenomena is probably due to a slight amount of luminescence of the tooth surface.

Figure 6:
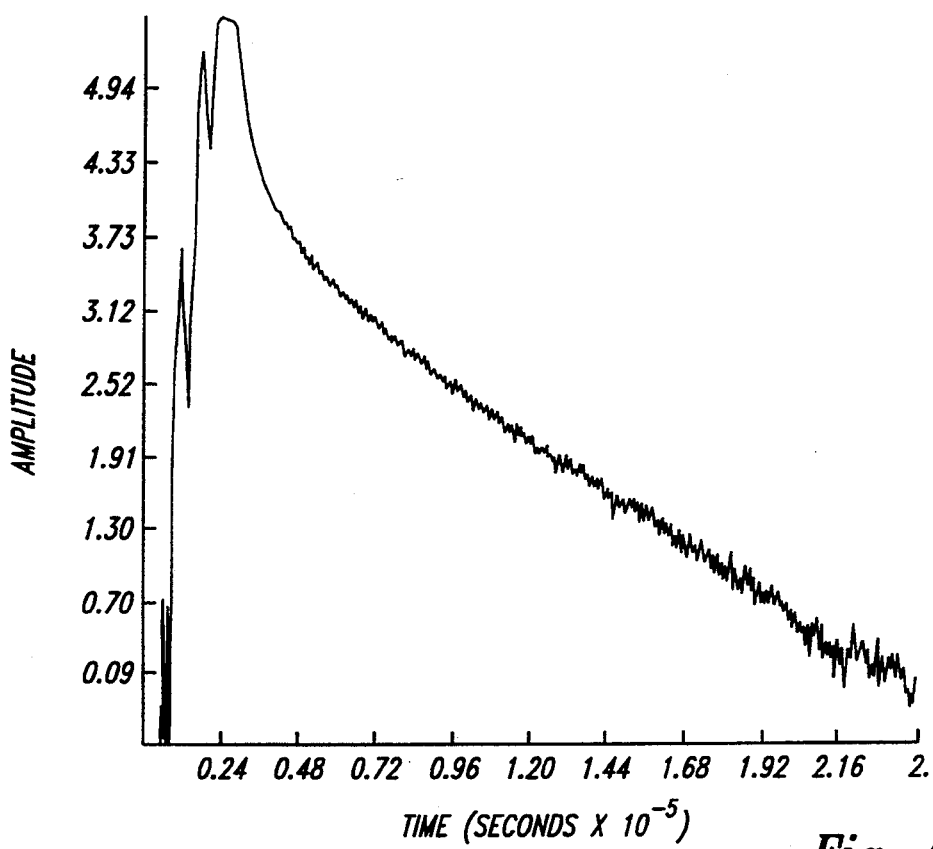
FIG. 6 is a graph of the intensity of electromagnetic radiation as a function of time from a probe used in the embodiment of FIG. 1 when the probe is in contact with a tooth site containing plaque or calculus.

FIG. 6 is a graph of the signal from the light detector subsystem 14 when the probe tip 32 is placed in contact with a tooth site containing a calculus deposit. It is apparent from a comparison between FIGS. 5 and 6 that the decay of the returned signal is markedly slower when a calculus or plaque deposit is present at a tooth site. Various parameters can be derived from this slower decay of the returned signal. For example, the time constant $\tau$ of the returned signal (i.e., the time required for the returned signal to decay to a predetermined percentage of its value at a predetermined time) can be used to provide an indication of the presence or absence of calculus. Also, since the amplitude of the returned signal decays slower in the presence of calculus or plaque, the intensity of the returned signal can be averaged over a predetermined interval and used to signal the presence or absence of plaque or calculus at a tooth site. For example, the data illustrated in the following Table 1 shows average intensity values and time constants for a number of measurements in which calculus or plaque is present and is not present:

TABLE 1

| Sample No. | $\tau$ | Intensity | Site |
|---|---|---|---|
| CALCULUS | | | |
| 1 | .7707 | 129.62 | |
| 2 | .7622 | 79.91 | |
| 3 | .7707 | 122.57 | |
| 4 | .7898 | 133.96 | |
| 5 | .7513 | 107.04 | |
| 6 | .7891 | 126.57 | |
| NON-CALCULUS | | | |
| 1 | .7040 | 59.57 | Normal Tooth |
| 2 | .7276 | 52.82 | Bloody Tissue |
| 3 | .7084 | 50.77 | Node on Tooth |
| 4 | .6717 | 49.49 | Serum |
| 5 | .7156 | 56.36 | Irregular Tooth |
| 6 | .7250 | 53.34 | Air |

The intensity, values shown in Table 1 were the average of samples taken during a period of from 3–7 microseconds after determination of an optical pulse. The time constant ($\tau$) data were taken during an interval of between 4–5 microseconds after determination of an optical excitation pulse, and specify the time required for the returned signal to decay to 10% of its value at the start of the period. The data in Table 1 demonstrates that the presence or absence of plaque or calculus can be readily determined from the intensity and time constant data.

Figure 7:
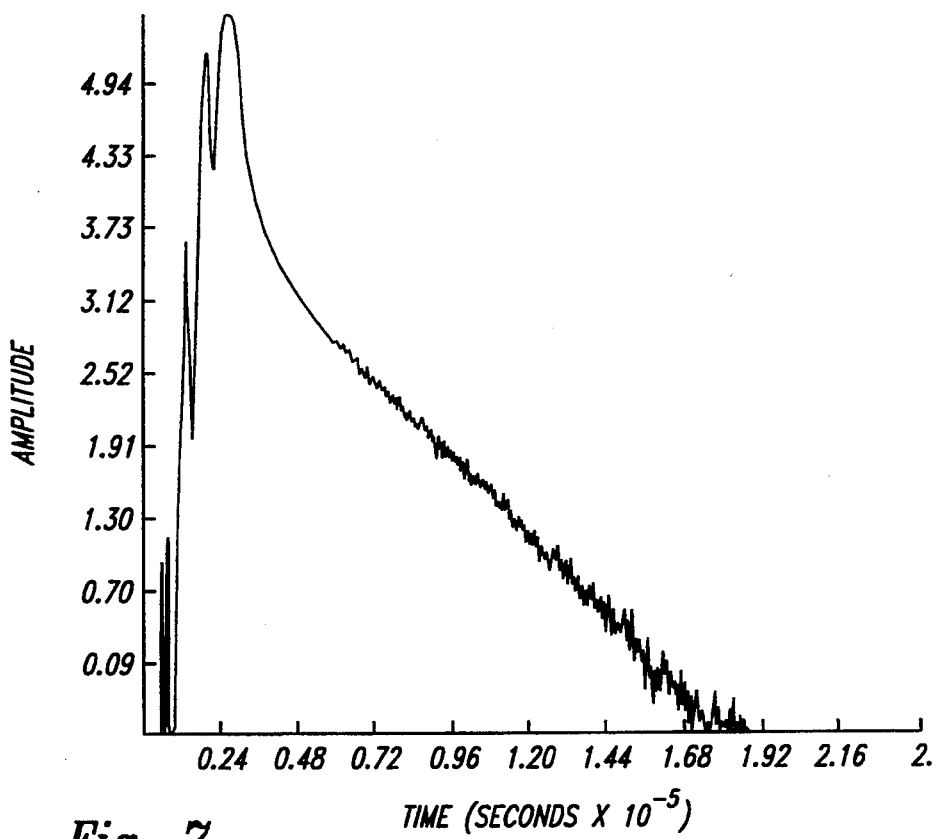
FIG. 7 is a graph of the intensity of electromagnetic radiation as a function of time from a probe used in the embodiment of FIG. 1 when the probe is in contact with the tooth site of FIG. 6 after the plaque or calculus has been removed from the site.

The validity of the discovery that plaque and calculus can be to detected using the inventive method and apparatus is illustrated in FIG. 7. FIG. 7 is a graph of the luminescence signal taken at the same tooth site that was used to generate the graph of FIG. 6 after the calculus deposit had been removed from that site. A comparison between FIGS. 5, 6 and 7 indicate that The luminescence signal has returned to the profile of a normal tooth site illustrated in FIG. 5 after the calculus had been removed.

The inventive method and apparatus thus easily allows plaque and calculus to be detected even subgingivally using a variety of light sources and light detectors and a variety of analysis techniques.

I claim:

1. A method of detecting presence of dental or calculus at a site on a tooth in an animal, comprising:
    generating a first electromagnetic radiation having a range of wavelengths and extending beyond 457 nm;
    coupling said first electromagnetic,, radiation to said site thereby illuminating said site with said electromagnetic radiation, said first electromagnetic radiation causing a second electromagnetic radiation to be returned from said site if dental plaque or calculus is present at said site;
    coupling said second electromagnetic radiation from said site to an analysis location outside, said body; and
    analyzing a predetermined characteristic of said second electromagnetic radiation to detect the presence of a dental plaque or calculus at said site.

2. The method of claim 1 wherein said first electromagnetic radiation has a range of wavelengths of between approximately 375 nm to 575 nm.

3. The method of claim 2 wherein said first electromagnetic radiation is generated by the step of:
    generating electromagnetic radiation having a broad range of wavelengths encompassing the range of between approximately 375 nm to 575 nm; and passing said electromagnetic radiation through a band pass filter having a pass-band between approximately 375 nm to 575 nm before coupling said electromagnetic radiation to said site.

4. The method of claim 2 further including the step of passing said second electromagnetic radiation through an optical filter prior to the step of analyzing a predetermined characteristic of said second electromagnetic radiation.

5. The method of claim 4 wherein said optical filter passes electromagnetic radiation having a wavelength of greater than approximately 600 nm.

6. The method of claim 1 wherein said first electromagnetic radiation and said second electromagnetic radiation are couplet to and from said site through an optical waveguide.

7. The method of claim 1 wherein said step of analyzing a predetermined characteristic of said second electromagnetic radiation includes the step of analyzing a characteristic related to the intensity of said second electromagnetic radiation.

8. The method of claim 7 wherein said step of analyzing a characteristic related to the intensity of said second electromagnetic radiation includes the step of determining the average intensity of said second electromagnetic radiation during a predetermined period after the termination of a pulse of said first electromagnetic radiation coupled to said site.

9. The method of claim 8 wherein said predetermined period during which the average intensity of said second electromagnetic radiation is determined is between approximately 3 microseconds and 7 microseconds after said first electromagnetic radiation pulse has terminated.

10. A method of detecting the presence of dental plaque or calculus at a site on a tooth in an animal, comprising:
generating a first electromagnetic radiation having a predetermined characteristic;
coupling said first electromagnetic radiation to said site thereby illuminating said site with said electromagnetic radiation, said first electromagnetic radiation causing a second electromagnetic radiation to be returned from said site if dental plaque or calculus is present at said site
coupling said second electromagnetic radiation from said site to an analysis location outside said body; and
analyzing a predetermined characteristic of said second electromagnetic radiation to detect the presence of a dental plaque of calculus at said site wherein said step of analyzing a predetermined characteristic of said second electromagnetic radiation including the step of analyzing a variation of the predetermined characteristic of said second electromagnetic radiation as a function of time.

11. The method of claim 10 wherein said time-related characteristic is a predetermined phosphorescent emission decay characteristic of said second electromagnetic radiation as a function of time after the termination of said first electromagnetic radiation being coupled to said site.

12. The method of claim 11 wherein said step of analyzing a predetermined phosphorescent emission decay characteristic of said second electromagnetic radiation includes the step of determining the rate of decrease in the intensity of said second electromagnetic radiation as a function of time during a predetermined period after said first electromagnetic radiation has been terminated.

13. The method of claim 12 wherein said predetermined period during which the rate of decrease in the intensity of said second electromagnetic radiation is determined is between approximately 4 microseconds and 5 microseconds after said first electromagnetic radiation has terminated.

14. The method of claim 10 wherein said first electromagnetic radiation is amplitude modulated at a predetermined frequency so that said second electromagnetic radiation is amplitude modulated at the same frequency if dental plaque or calculus are present at said site, and wherein said time-related characteristic is the difference between the phase of the amplitude modulation of said first electromagnetic radiation and the phase of the amplitude modulation of said second electromagnetic radiation.

15. A system for detecting the presence of dental plaque or calculus at a site on a tooth in an animal, comprising:
a source of a first electromagnetic radiation having a range of wavelengths extending beyond 457 nm, said first electromagnetic radiation being coupled to said site thereby illuminating said site with said electromagnetic radiation, said first electromagnetic radiation causing a second electromagnetic radiation to be returned from said site if dental plaque or calculus is present at said site; and
analyzing means receiving said second electromagnetic radiation for analyzing a predetermined characteristic of said second electromagnetic radiation to detect the presence of a dental plaque or calculus at said site.

16. The detecting system of claim 15 wherein said first electromagnetic radiation has a range of wavelengths of between approximately 375 nm to 575 nm.

17. The detecting system of claim 16 wherein said source of first electromagnetic radiation comprises:
a source of electromagnetic radiation having a broad range of wavelengths encompassing the range of between approximately 375 nm to 575 nm; and
a band pass filter filtering said electromagnetic radiation before said radiation is coupled to said site, said band pass filter having a pass-band between approximately 375 nm to 575 nm.

18. The detecting system of claim 16, further including an optical filter positioned between said site and said analyzing means so that said second electromagnetic radiation passes through said optical filter prior being analyzed by said analyzing means.

19. The detecting system of claim 18 wherein said optical filter passes electromagnetic radiation having a wavelength of greater than approximately 600 nm.

20. The detecting system of claim 15 wherein said system further includes an optical waveguide coupling said first electromagnetic radiation to said site and said second electromagnetic radiation from said site.

21. The detecting system of claim 15 wherein said predetermined characteristic analyzed by said analyzing means if related to the intensity of said second electromagnetic radiation.

22. The detecting system of claim 21 wherein said source of first electromagnetic radiation generates a pulse of said radiation, and wherein said characteristic related to the intensity of said second electromagnetic radiation is the average intensity of said second electromagnetic radiation during a predetermined period after the termination of a pulse of said first electromagnetic radiation coupled to said site.

23. The detecting system of claim 22 wherein said predetermined period during which the average intensity of said second electromagnetic radiation is determined is between approximately 3 microseconds and 7 microseconds after said first electromagnetic radiation pulse has terminated.

24. A method of detecting the presence of dental plaque or calculus at a site on a tooth in an animal, comprising:
   generating a first electromagnetic radiation having a predetermined characteristic;
   coupling said first electromagnetic radiation to said site thereby illuminating said site with said electromagnetic radiation, said first electromagnetic radiation causing a second electromagnetic radiation to be returned from said site if dental plaque of calculus is present at said site;
   coulping said second electromagnet radiaton from said site to analysis location outside said body; and
   analyzing a predetermined characteristic of said second electromagnetic radiation to detect the presence of a dental plaque or calculus at said site wherein said analyzing means analyzes a variation of the predetermined characteristic of said second electromagnetic variation as a function of time.

25. The detecting system of claim 24 wherein said source of first electromagnetic radiation generates a pulse of said radiation, and wherein said time-related characteristic is a predetermined phosphorescent emission decay characteristic of said second electromagnetic radiation as a function of time after the termination of said first electromagnetic radiation pulse.

26. The detecting system of claim 25 wherein said analyzing means determines the rate of decrease in the intensity of said second electromagnetic radiation as a function of time during a predetermined period after said first electromagnetic radiation pulse has terminated.

27. The detecting system of claim 26 wherein said predetermined period during which the rate of decrease in the intensity of said second electromagnetic radiation is determined is between approximately 4 microseconds and 5 microseconds after said first electromagnetic radiation pulse has terminated.

28. The detecting system of claim 24 wherein said source of first electromagnetic radiation amplitude modulates said electromagnetic radiation at a predetermined frequency so that said second electromagnetic radiation is amplitude modulated at the same frequency if dental plaque or calculus are present at said site, and wherein said time-related characteristic analyzed by said analyzer means is the difference between the phase of the amplitude modulation of said first electromagnetic radiation and the phase of the amplitude modulation of said second electromagnetic radiation.

* * * * *

UNITED STATES PATENT AND TRADEMARK OFFICE
CERTIFICATE OF CORRECTION

PATENT NO. : 5,382,163
DATED : January 17, 1995
INVENTOR(S) : David L. Putnam

It is certified that error appears in the above-identified patent and that said Letters Patent is hereby corrected as shown below:

In column 8, claim 1, line 43, after "detecting" and before "presence", please insert --the--.

In column 8, claim 1, line 43, after "dental" and before "or", please insert --plaque--.

In column 8, claim 1, line 49, after "electromagnetic" and before "radiation", please delete --"--.

In column 9, claim 10, line 52, please delete "of" and substitute therefor --or--. (2nd occurr.)

In column 10, claim 21, line 61, please delete "if" and substitute therefor --is--.

In column 11, claim 24, line 18, please delete "of" and substitute therefor --or--.

In column 11, claim 24, line 21, after "to" and before "analysis", please insert --an--.

Signed and Sealed this

Nineteenth Day of September, 1995

*Attest:*

BRUCE LEHMAN

*Attesting Officer*            *Commissioner of Patents and Trademarks*